(12) United States Patent
Duffy et al.

(10) Patent No.: US 8,968,233 B2
(45) Date of Patent: Mar. 3, 2015

(54) ARTERIOVENOUS SHUNT HAVING A MOVEABLE VALVE

(75) Inventors: Niall Duffy, Ballygluinin (IE); Kevin O'Sullivan, Tralee (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 561 days.

(21) Appl. No.: 13/365,994

(22) Filed: Feb. 3, 2012

(65) Prior Publication Data

US 2013/0204176 A1   Aug. 8, 2013

(51) Int. Cl.
*A61M 5/00* (2006.01)

(52) U.S. Cl.
USPC ............................................................ 604/9

(58) Field of Classification Search
USPC .............. 604/8, 9, 33, 34; 606/109, 151, 153, 606/155; 623/1.1, 1.11, 1.12, 1.14–1.16, 623/1.2, 1.24, 1.25, 1.27, 1.3, 1.32, 1.36
See application file for complete search history.

(56) References Cited

U.S. PATENT DOCUMENTS

| | | | |
|---|---|---|---|
| 3,998,222 A | 12/1976 | Shihata | |
| 6,616,675 B1 | 9/2003 | Evard et al. | |
| 7,473,240 B2 | 1/2009 | Peavey | |
| 7,846,172 B2 | 12/2010 | Makower | |
| 2005/0277964 A1 | 12/2005 | Brenneman et al. | |
| 2007/0055296 A1 | 3/2007 | Stergiopulos | |
| 2008/0281249 A1 | 11/2008 | Gertner | |
| 2009/0062669 A1 | 3/2009 | Akingba | |
| 2010/0030322 A1 | 2/2010 | Lee et al. | |
| 2010/0056978 A1 | 3/2010 | Machan | |

FOREIGN PATENT DOCUMENTS

WO   2009152488 A1   12/2009

OTHER PUBLICATIONS

Faul, John L. M.D. and Sievert, Horst M.D., Percutaneous Creation of Arteriovenous Shunts, Vascular Disease Management, vol. 5, Sep. 1, 2008 (http://vasculardiseasemanagement.com/content/percutaneous-creation-arteriovenous-shunts).

*Primary Examiner* — Melanie Hand

(57) ABSTRACT

An arteriovenous shunt assembly including a shunt having a hollow bore between open first and second ends thereof and a valve slidably disposed through the hollow bore. The valve includes means for retaining the valve in a closed position or in any of various selected open positions that provide corresponding different rates of blood flow through the shunt assembly. In some embodiments, the AV shunt assembly is self-expandable from a collapsed tow-profile configuration employed during transluminal delivery. The valve position in the hollow bore may be adjusted in vivo by inflating a catheter balloon in a blood vessel to bear against an end of the valve. Methods for using the shunt assembly are also disclosed.

20 Claims, 12 Drawing Sheets

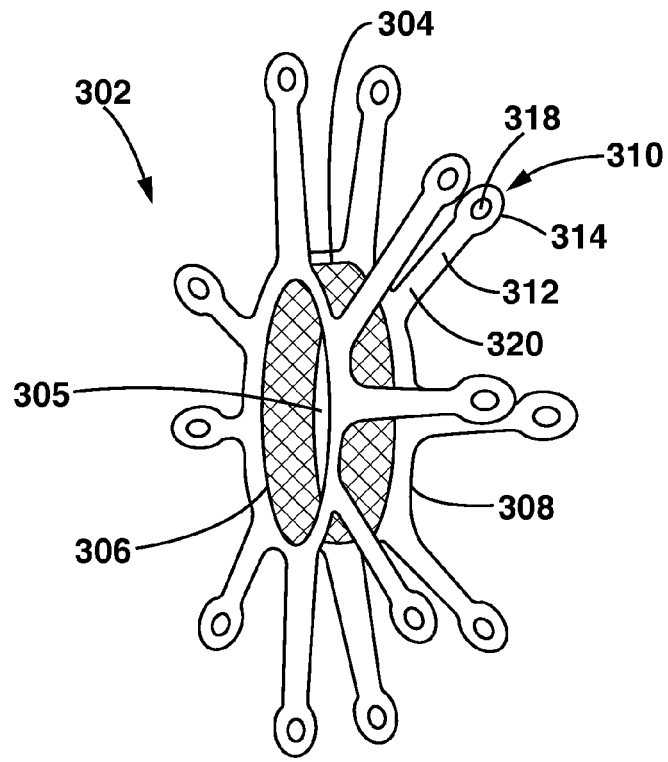
FIG. 3
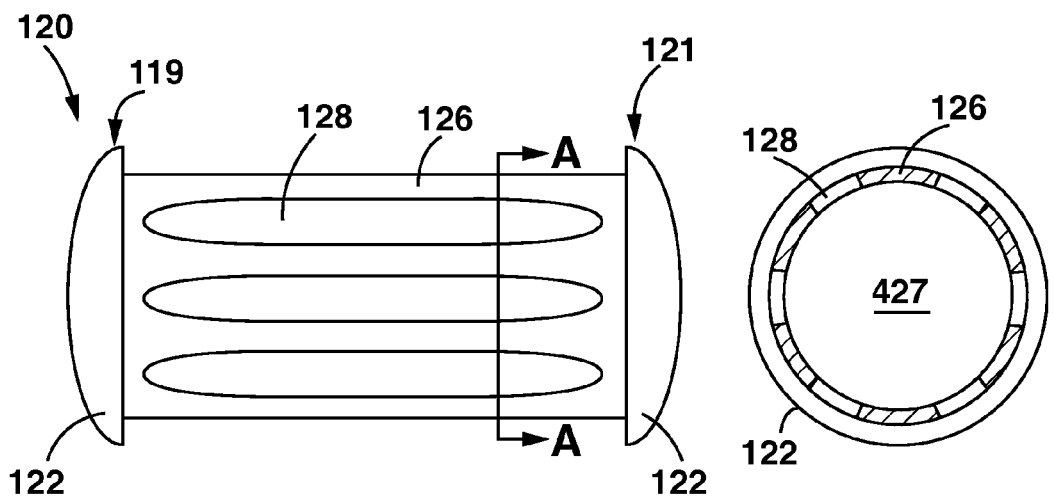
FIG. 4  FIG. 4A

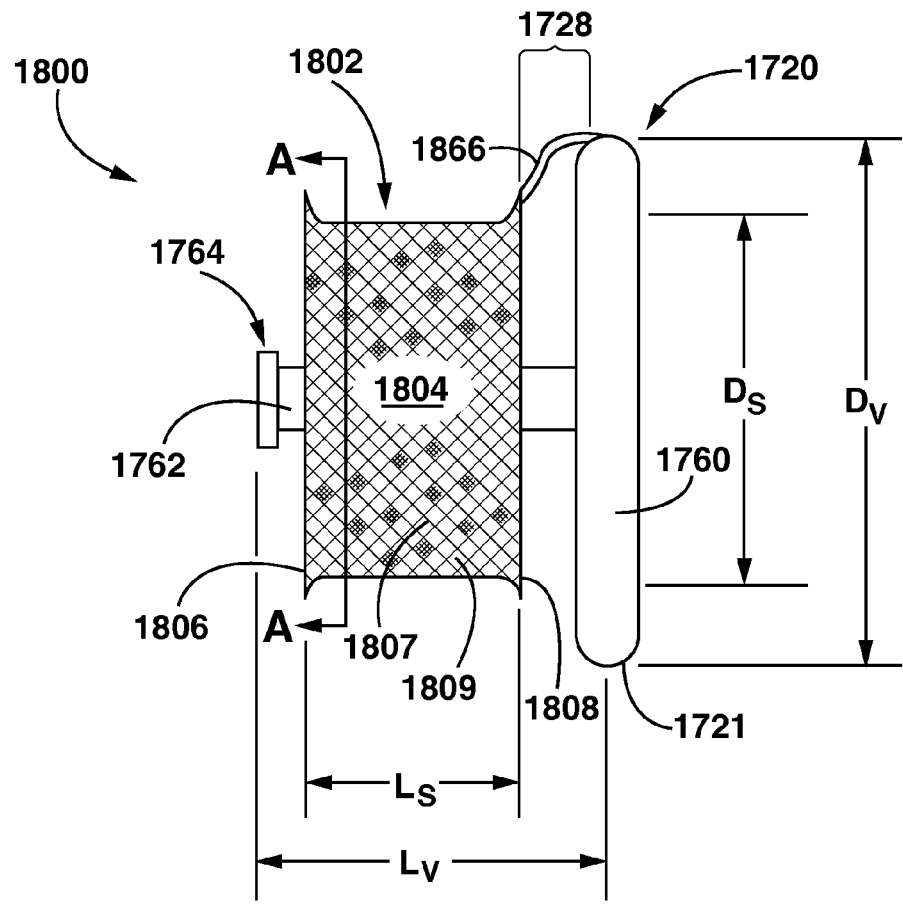
FIG. 17
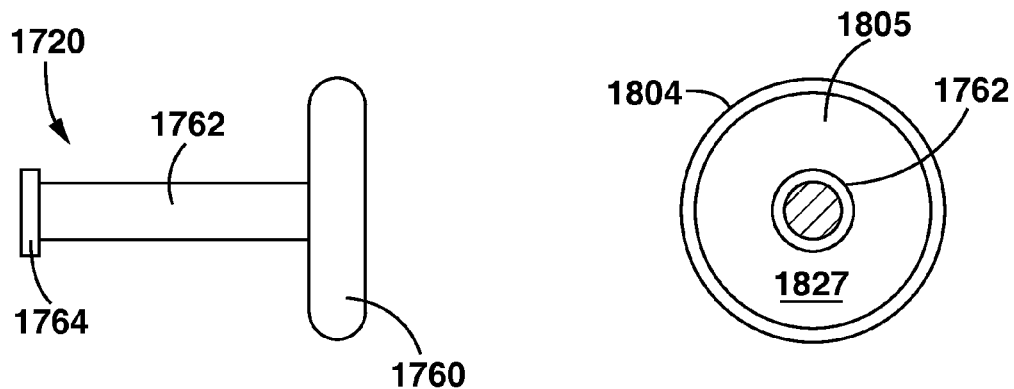
FIG. 18  FIG. 17A

ARTERIOVENOUS SHUNT HAVING A MOVEABLE VALVE

FIELD OF THE INVENTION

The invention relates to an implantable arteriovenous (AV) shunt assembly having a shunt and a movable valve disposed therein for adjusting the rate of blood flow through the assembly.

BACKGROUND OF THE INVENTION

In modern medicine there are numerous treatments in which it is desirable to create shunts or flow-through connections between blood vessels and/or other anatomical structures of the body. Such treatments include, for example, hemodialysis, hemofiltration, hemodiafiltration, plasmapheresis, and extracorporeal membrane oxygenation (ECMO). In many cases, open surgical techniques have been used to form anatomic connections or fistulas between adjacent vessels of body structures. More recently, percutaneous catheter-based techniques and devices have been developed for creating channels or passageways, e.g., shunts between adjacent vessels or anatomical structures.

In addition to the above-listed treatments, arteriovenous (AV) shunt devices have been proposed for treating chronic obstructive pulmonary disease (COPD) and drug-resistant hypertension. COPD, also called chronic obstructive airway disease, is a syndrome that may be caused by a number of different diseases, all of which damage the alveoli and bronchioles, leading to impaired lung function. These diseases include asthmatic bronchitis, chronic bronchitis (with normal airflow), chronic obstructive bronchitis, and emphysema. As the alveoli and bronchial tubes are destroyed, the remaining healthy lung tissue must work harder to provide the required amount of blood oxygenation. The need for more air leads to lung over-inflation. As the lung over-expands, it gradually enlarges, completely filling the chest cavity and causing a sense of shortness of breath. The lung eventually loses its elasticity and the combination of a larger, less elastic lung and damaged, nonfunctioning tissue leads to slower airflow into and out of the lung, resulting in the feeling in the patient of an obstructed airway.

One manner of treating CORD is oxygen therapy, which requires a patient to remain near a stationary oxygen source or carry a bulky portable oxygen source when away from home or a treatment facility. Understandably such oxygen therapy has many disadvantages. One surgical treatment that has been proposed for treating patients with COM is lung reduction surgery. Such surgery, however, can be used on only a small percentage of the total patient population, requires long recovery times, and does not always provide a clear patient benefit.

Arteriovenous (AV) shunt devices for treating COPD provide a fistula between an artery and a vein that are anatomically adjacent to each other. The approach is to create an arteriovenous fistula by implanting a shunt-like device between two major blood vessels in, for example, the leg, utilizing cardiovascular reserve to overcome respiratory insufficiency and improve oxygenation to the lungs. The shunt allows oxygen-rich blood from the artery to flow to the vein and thereby increases the oxygen content of the blood returning to the heart and lungs, which in turn is considered to benefit a patient suffering from COPD. The implantation of the shunt can increase cardiac output by about one liter per minute, without impacting heart rate or oxygen consumption.

Such AV shunt devices have been suggested to be implanted via an open surgical procedure or via a minimally invasive intravascular surgical procedure, depending on the specific arterial and venous locations that are to be connected by the AV shunt. A need continues to exist in the art for an AV shunt that may be quickly and simply delivered and deployed via a minimally invasive intravascular procedure. In addition, after the AV shunt is implanted, the flow through the shunt may need to be adjusted in order to maximize the benefit or improvement to the patient's condition. Accordingly, embodiments hereof relate to an AV shunt assembly that is delivered in a minimally invasive procedure to create a fistula between adjacent vascular structures, whereby the flow through the shunt may be selectively adjusted in vivo.

BRIEF SUMMARY OF THE INVENTION

Embodiments hereof relate to an arteriovenous shunt assembly including a tubular shunt body and a valve slidably disposed therein. The shunt body defines a hollow bore between a first end and a second end. The valve extends through the hollow bore of the shunt and has at least a first end cap sized to selectively close one end of the tubular shunt. The axial position of the valve relative to the shunt may be incrementally changed between an open position in which the first cap is spaced from one end of the tubular shunt and a closed position in which the first cap is sealed against the end of the tubular shunt. Various open valve positions may permit corresponding rates of blood flow through the hollow bore of the shunt, and the closed position prevents blood flow through the hollow bore of the shunt.

In one embodiment, a tubular valve body is longer than the body of the shunt, with end caps closing the ends of the valve body. At least one elongate side orifice is formed through the valve body. The valve body may be longitudinally translated within the shunt body in order to position the valve in a selected location between an open position and a closed position. In the open position, the side orifice extends beyond both ends of the shunt body to permit flow through the valve body and thus through the shunt. In the closed position, no side orifice extends beyond one end of the shunt body and/or one valve end cap is sealingly pressed against an end of the shunt body.

In another embodiment, a valve is longer than the shunt and has a disk mounted on a stem that extends through the hollow bore of the shunt. The disk is also coupled to an end of the shunt via a connector formed from a plastically deformable material. When the valve is axially translated between different positions in the shunt body, the connector plastically deforms in order to maintain the selected valve position and the associated flow rate through the shunt assembly.

Embodiments hereof also relate to a method for forming a connection between first and second body vessels. A shunt assembly is intravascularly delivered in a collapsed configuration to a tissue track formed from the first vessel to the second vessel. The shunt assembly includes a shunt having a tubular body and a valve extending through and beyond the ends of the shunt. The shunt assembly is radially expanded in the tissue track such that one end of the valve is in a first vessel, and the other end of the valve is in a second vessel. A force is selectively applied to one end of the valve in order to longitudinally shift the valve between an open position that permits blood flow through the hollow bore of the shunt and a closed position that prevents blood flow through the hollow bore of the shunt. It should be noted that the "open" valve configurations or positions described in the above embodiments may comprise a range of valve positions between fully closed and fully open to permit the clinician to selectively adjust the rate of blood flowing through the shunt assembly.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is a perspective view of a shunt according to another embodiment hereof, wherein the shunt includes a plurality of radially expandable anchors.

FIG. 4 is a side view of the valve of FIG. 1 removed from the AV shunt assembly.

FIG. 4A is a cross-sectional view of the valve of FIG. 4 taken along line A-A.

FIGS. 9A, 9B, 9C are perspective views illustrating incremental movement of a valve within a shunt, while

FIG. 17 is a side view of another AV shunt assembly according to an embodiment hereof.

FIG. 17A is a transverse cross-sectional view of the shunt assembly of FIG. 17 taken along line A-A.

FIG. 18 is a side view of the valve of FIG. 17 removed from the AV shunt assembly.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, the term "self-expanding" is used in the following description with respect to components comprising a material that has a mechanical memory to return the component to an expanded deployed configuration from a compressed or constricted delivery configuration. Non-exhaustive examples of such shape memory materials include spring temper stainless steel, a pseudo-elastic metal such as a nickel titanium alloy (nitinol), an elastic polymer, or a so-called super alloy, which may have a base metal of nickel, cobalt, chromium, or other metal. Mechanical shape memory may be imparted to a wire or tubular structure by thermal treatment to achieve a spring temper in stainless steel, for example, or to set a shape memory in a susceptible metal alloy, such as nitinol, or a shape memory polymer such as any of the polymers disclosed in U.S. Pat. Appl. Pub. No. 2004/0111111 to Lin, which is incorporated by reference herein in its entirety.

The following detailed description is merely exemplary in nature and is not intended to limit the invention or the application and uses of the invention. Although the description of the invention is in the context of an AV shunt for the treatment of a patient suffering from COPD and related conditions, embodiments hereof may also be used as a shunt for treatment of other conditions and/or may be used to bridge any anatomical lumens or conduits where it is deemed useful. Furthermore, there is no intention to be bound by any expressed or implied theory presented in the preceding technical field, background, brief summary or the following detailed description.

Figure 1:
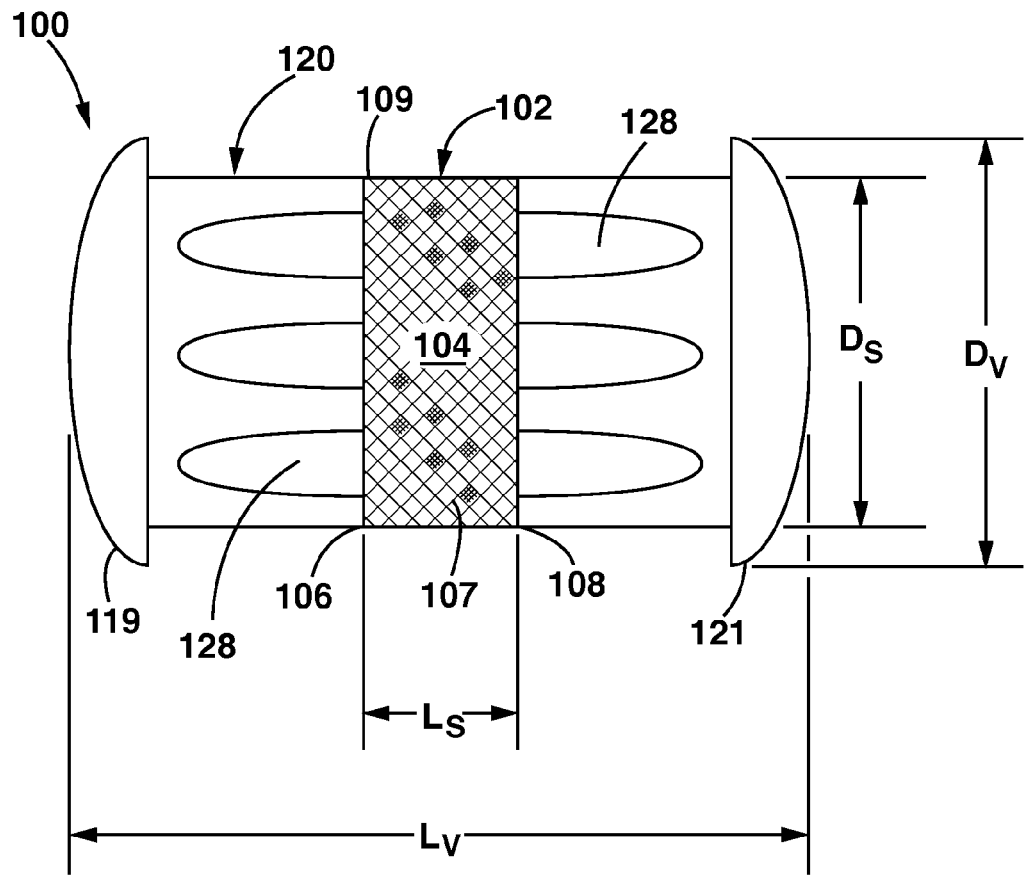
FIG. 1 is a side view of an AV shunt assembly according to an embodiment hereof, the AV shunt assembly including a shunt and a movable valve disposed therein.

Embodiments hereof are directed to apparatuses and methods for creating an artificial arteriovenous (AV) fistula or connection between an artery and an adjacent vein with an AV shunt assembly that includes a shunt and a movable valve disposed within the shunt for selectively controlling blood flow through the shunt. Referring to FIG. 1, an AV shunt assembly 100 includes a conduit or shunt 102 and a movable valve body 120. Shunt 102 has a tubular body 104 defining a hollow bore 205 (shown in FIG. 2) extending between an open first end 106 and an open second end 108. Movable valve 120 is disposed within hollow bore 205 of shunt 102 and has a length $L_V$ that is longer than a length $L_S$ of shunt body 104. In the valve position shown, a first end 119 of valve 120 extends beyond first end 106 of shunt body 104 and a second end 121 of valve 120 extends beyond second end 108 of shunt body 104. Movable valve 120 may be shifted or translated in an axial or longitudinal direction back and forth within shunt 102 in order to regulate the amount of flow through AV shunt assembly 100, as will be described in more detail herein. Movable valve 120 thus allows a physician to selectively adjust or control the flow through the shunt assembly in vivo. Adjustments of the flow may be necessary to achieve positive effects/improvement in the patient's condition, i.e., to maximize blood oxygenation in the treatment of COPD. Further, having the ability to adjust the rate of flow post implantation of the AV shunt gives the physician the ability to make performance adjustments over time without removing the shunt.

Figure 2:
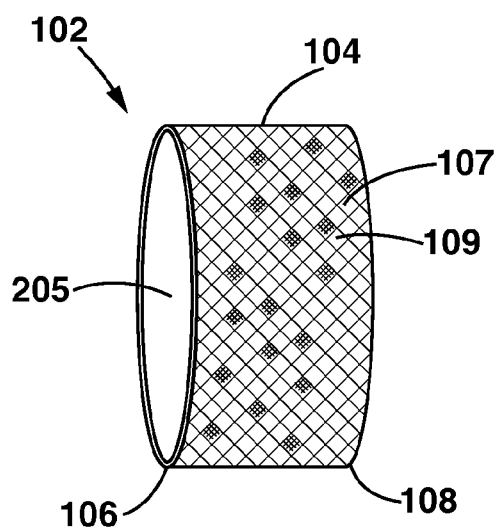
FIG. 2 is a perspective view of the shunt of FIG. 1 removed from the AV shunt assembly.

Referring to FIG. 2, shunt 102 is shown removed from AV shunt assembly 100. Several embodiments for the tubular body 104 of the shunt are discussed herein, and it will be understood by one of ordinary skill in the art that the shunt body may have various other configurations that are suitable for forming a connection or tissue track between two adjacent body lumens, such as an artery and a vein. In one embodiment, tubular body 104 is a radially expandable flexible stent graft. The stent-like component may be constructed from a mesh or lattice scaffolding or stent 107. Stent 107 is formed from a self-expanding material that returns to an expanded deployed configuration from a compressed or constricted delivery configuration. Stent 107 allows shunt 102 to be compressed and constrained in a radially collapsed state but, when unconstrained, shunt 102 will assume an expanded diameter $D_S$ as seen in FIG. 1. Delivery systems and processes for deploying self-expanding AV shunts as described herein are discussed in further detail below.

Graft material 109 is attached to stent 107 to create a conduit or fluid passageway through shunt body 104. Graft material 109 may be expanded polytetrafluoroethylene (ePTFE) or a low-porosity knit or woven polyester fabric, either of which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, graft material 109 could also be a natural material such as pericardium or another membranous tissue such as intestinal submucosa.

In one embodiment, shunt 102 may include one or more radially expandable support arms or anchors for securing AV shunt assembly 100 at the target location. For example, as shown in FIG. 3, a shunt 302 is shown having a tubular body 304 extending between an open first end 306 and an open second end 308 to define a hollow bore 305 there through. As described above with respect to tubular body 104, tubular body 304 is a radially expandable cylindrical component and may be a flexible stent graft made of a mesh tubular stent having graft material enclosing or lining the stein. Shunt 302 includes a plurality of anchors 310 that extend radially from both first and second ends 306, 308 of tubular body 304 when deployed. Each anchor 310 is generally shown in the figures as an elongated tab or finger 312 having a rounded tip 314. However, the anchors may have other configurations such as U-shaped, V-shaped, semi-circular, rectangular, oblong, or the like, and may be considerably longer, shorter, wider, or narrower than shown. One or more rounded tips 314 may be wider than their respective fingers 312 and may also include an opening or eyelet 318 formed therein. Tips 314 may thus be designed for engagement with a delivery system, as will be described in further detail herein with respect to FIG. 12. Each anchor 310 is coupled to either first end 306 or second end 308 of shunt 302. In one embodiment, anchors 310 are formed separately and mechanically coupled to shunt 302 at junction 320 via any suitable method, including welding, soldering, or by a mechanical method. In another embodiment, anchors 310 and the stent of shunt 302 are formed as a pre-connected unitary structure, such as by laser cutting or etching material from a hollow tube or sheet. Anchors 310 are formed from a shape memory material in order to transform elastically between an initial straightened delivery configuration described in more detail herein with respect to FIG. 11 and the final radially-extending deployed configuration shown in FIG. 3.

Figure 19:
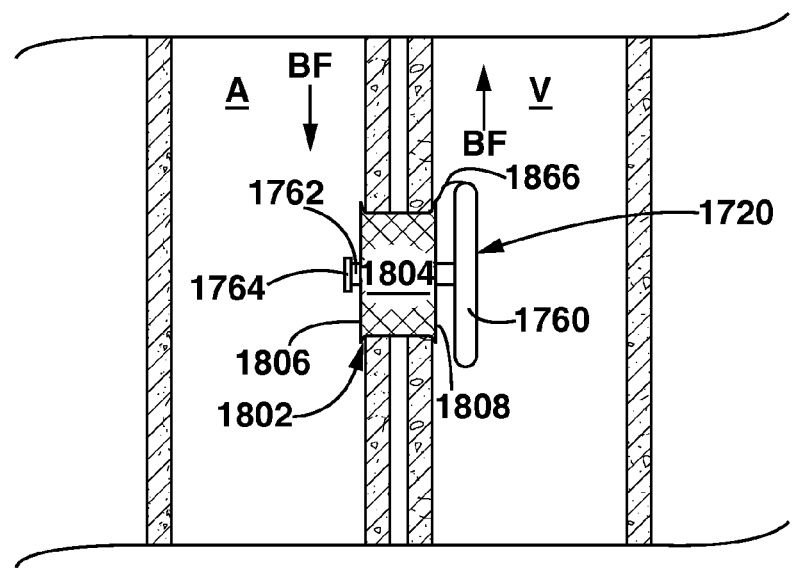
FIGS. 19-20 are side view illustrations showing open and closed positions of the AV shunt assembly of FIG. 17 in vivo.
Figure 20:
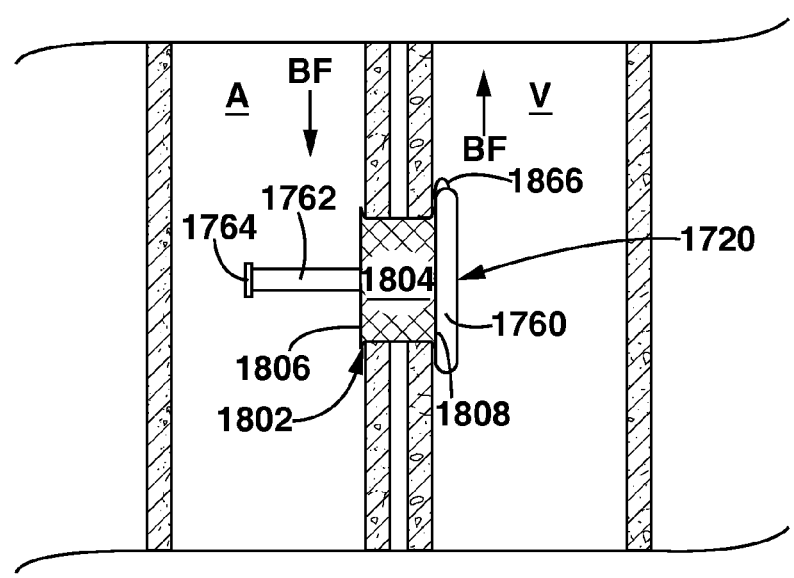

In a variation of shunts 102, 302, shunt body 104, 304 may lack graft covering 109. Such an embodiment may be suitable where an artery and a vein are contiguous such that the AV shunt forming a fistula therebetween requires no graft-type fluid conduit to span a gap between the two blood vessels. FIGS. 10, 12 and 13-16 illustrate such a patient anatomy. Where a space between an adjacent artery and vein needs to be traversed, as shown in FIGS. 19 and 20, the stent graft type of shunt body is more suitable for forming a fistula without leaking blood.

FIG. 4 depicts valve 120 removed from AV shunt assembly 100. Valve 120 has a cylindrical tubular body 126 defining a lumen 427 (shown in FIG. 4A) therethrough that is closed on first and second ends 119, 121 by end caps 122. Tubular body 126 includes a plurality of longitudinally extending slots or orifices 128 formed through the wall thereof to permit fluid communication with lumen 427 from outside of valve body 126. In an embodiment, orifices 128 extend substantially the entire length of tubular body 126 and are circumferentially spaced apart around tubular body 126. As shown in FIG. 1, valve tubular body 126 is slidingly disposed within shunt body 104 such that first and second ends of orifices 128 may be longitudinally positioned to provide fluid flow through lumen 427 of valve 120. Valve body 126 makes a light interference fit, also called a friction fit or a sliding fit within shunt bore 205 to maintain the valve position as selected or adjusted by the clinician to optimize the flow of oxygenated blood through shunt assembly 100, as discussed elsewhere herein. End caps 122 have an outer diameter $D_V$ that is equal to or greater than diameter $D_S$ of bore 205 in shunt body 104. End caps 122 act as stops for preventing valve 120 from disengaging with shunt 102. As such, when valve body 126 is slid or longitudinally shifted within shunt body 104 such that a respective end cap 122 abuts against either the first or second end 106, 108 of shunt 102, valve 120 is not permitted to slide out of shunt 102. Orifices 128 may be molded-in or removed portions of the wall of tubular body 126. In one embodiment, valve 120 may include between four and eight longitudinally extending orifices 128. Although shown as straight slots having rounded ends, orifices 128 may be other shapes and sizes, as discussed further herein regarding the operation and adjustment of the valve with respect to FIGS. 9A-10C.

Figures 5, 5A:
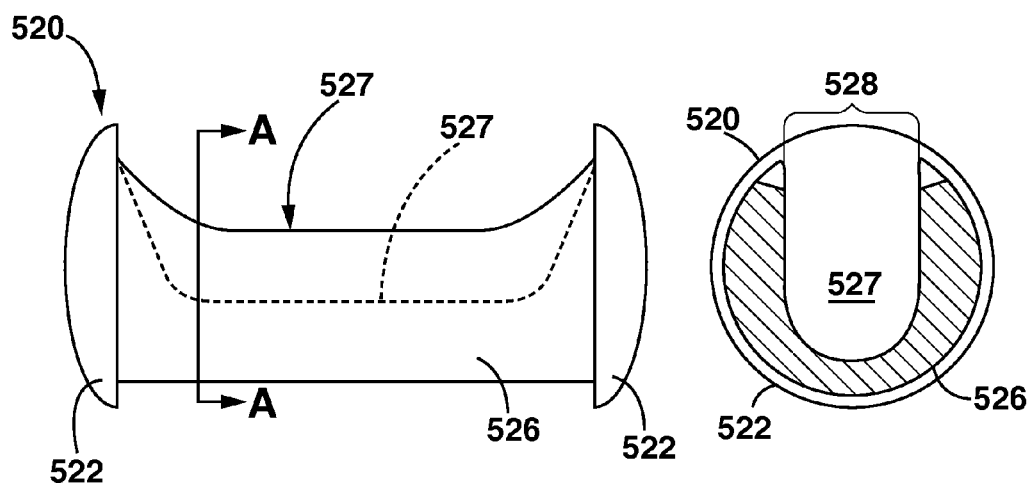
FIG. 5 is a side view of a valve according to another embodiment hereof, wherein the valve includes a solid body having a longitudinal trough.
FIG. 5A is a transverse cross-sectional view of the valve of FIG. 5 taken along line A-A.

FIGS. 5 and 5A illustrate another embodiment of a valve 520 wherein a cylindrical valve body 526 has a trough 527 formed therein to serve the same fluid communication function as lumen 427 in the previous valve embodiments. End caps 522 are formed with or attached to valve body 526 to act as longitudinal travel stops. Trough 527 may extend substantially the entire length of valve body 526 and has an orifice 528 extending along one side of body 526 to permit fluid communication with the trough from outside of body 526. Valve tubular bodies according to embodiments described above are formed from a shape memory material such that the valves return to their expanded deployed configurations from their compressed or constricted delivery configurations. For example, valve body 526 may be formed from an elastic or elastomeric material into a solid body or closed-cell foam body. Trough 527 may be molded or cut into the otherwise solid body 526.

Figure 6:
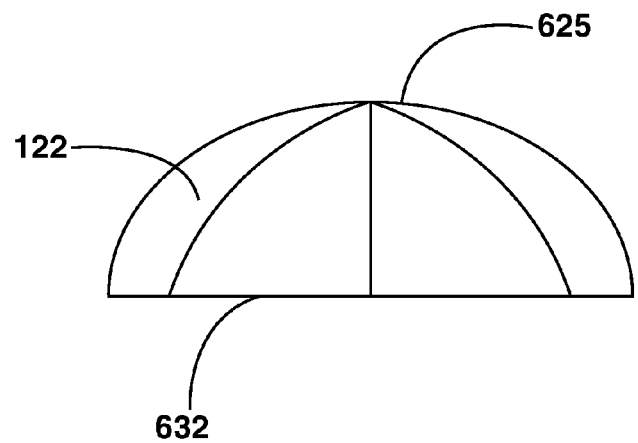
FIG. 6 is a side view of an end cap of the valve of FIG. 4.

FIG. 6 illustrates end cap 122 removed from valve body 126. End cap 122 has a rounded top surface 625 and an opposing, relatively flat bottom surface 632 for attachment to an end of tubular valve body 126. In one embodiment, end cap 122 is a molded component formed from a polymeric material that blocks flow there through. For example, end cap 122 may be formed from an elastic or elastomeric material into a solid body or closed-cell foam body. In another embodiment (not shown), end caps 122 may be formed from a surgical mesh material mounted, e.g., sutured to a self-expanding wire frame.

Figure 7:
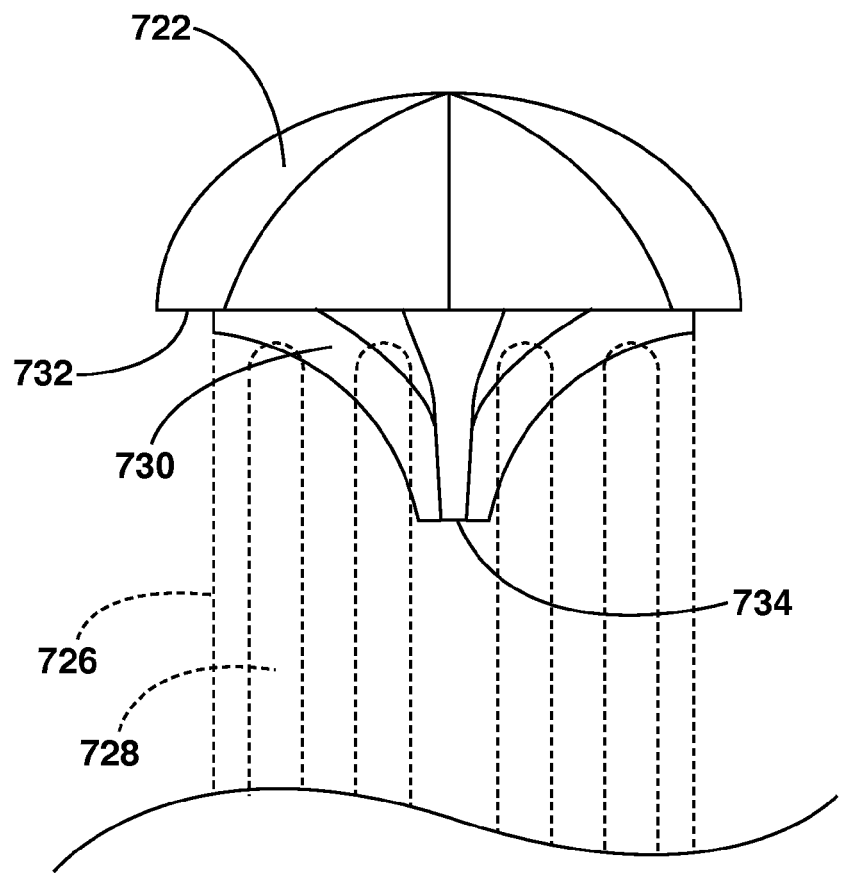
FIG. 7 is a partial side view of a valve according to another embodiment hereof, wherein the end cap includes a plurality of flow directing elements extending into the valve lumen.
Figure 8:
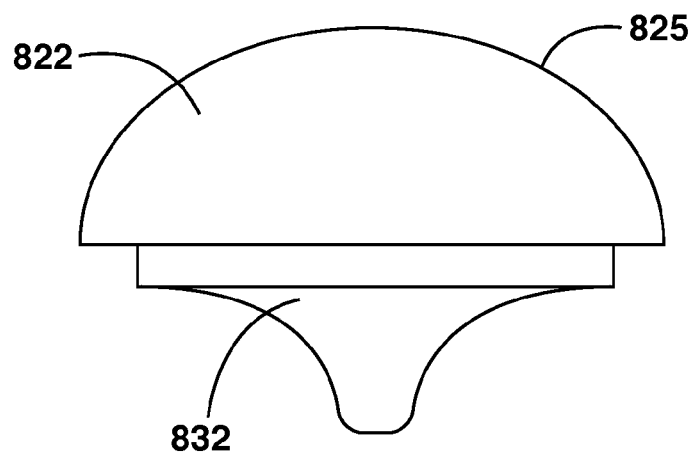
FIG. 8 is a side view of an end cap according to another embodiment hereof, wherein the end cap is a unitary molded component that includes a rounded top surface and an opposing curved bottom surface.

Referring to FIGS. 7 and 8, a bottom surface of an end cap may include one or more flow directing elements for extending within a lumen of the valve body. In FIG. 7, a plurality of flow directing elements 730 are coupled to a relatively flat bottom surface 732 of end cap 722. First ends of flow directing elements 730 are disposed about and coupled near an outer edge of end cap 722, and second ends of flow directing elements 730 gather together as shown at tip 734, where they may optionally be connected. Flow directing elements 730 may be sloping, concave, or curved shapes that serve to improve the hemodynamics of blood flow through the valve. Flow directing elements 730 extend sufficiently within lumen 427 to substantially block fluid flow entering slots 728 from passing transversely through the valve body 726, which is shown in phantom in FIG. 7. As shown in FIG. 7, in one embodiment, flow directing elements 730 may be approximately equally spaced apart around the perimeter of end cap 722. The number of flow directing elements 730 may vary depending upon application, and in one embodiment may include between three and ten segments. In one embodiment, flow directing elements 730 are formed separately and attached to end cap 722 via any suitable method, including adhesive or thermal bonding. In another embodiment, flow directing elements 730 and end cap 722 are pre-formed as a unitary structure, as by molding. In the embodiment of FIG. 8, end cap 822 is a unitary molded component that includes a rounded top surface 825 and an opposing curved bottom surface 832. Curved bottom surface 832 mimics the profile of flow directing elements 730 to improve the hemodynamics of blood flow through the valve.

Figure 9A:
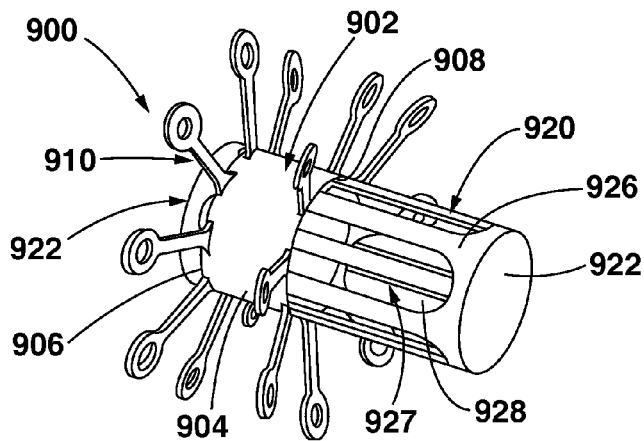
Figure 9B:
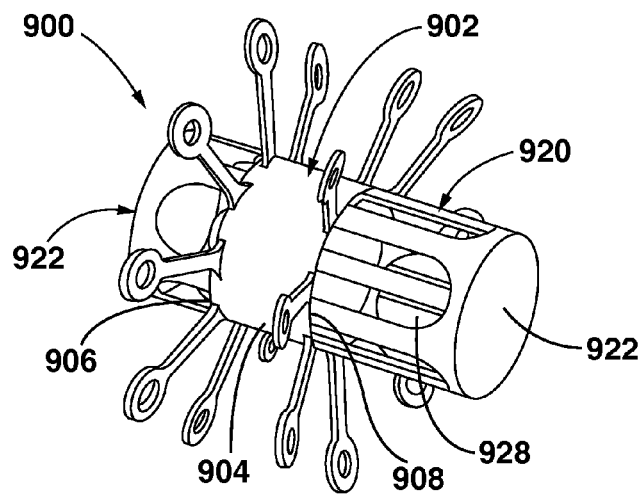
Figure 9C:
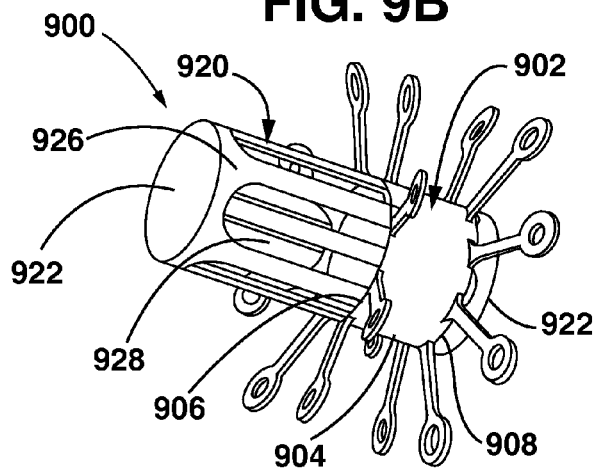
Figure 10A:
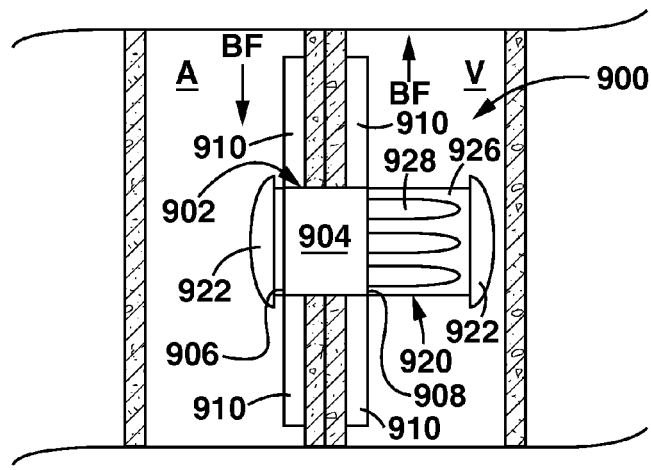
FIGS. 10A, 10B, 10C are corresponding side view illustrations showing incremental movement of the valve within the shunt in vivo.
Figure 10B:
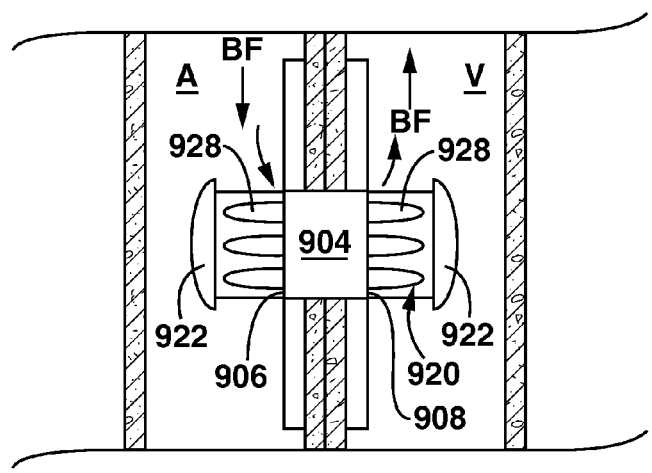
Figure 10C:
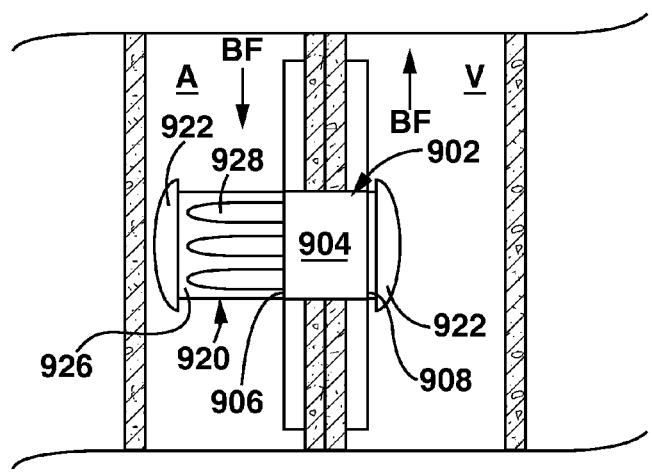

As described above, the valve structure may be shifted or translated back and forth in a longitudinal direction within the shunt in order to regulate the amount of flow through the shunt assembly. FIGS. 9A, 9B, and 9C are perspective views illustrating an AV shunt assembly 900 with incremental movement of a valve 920 within a shunt 902 thereof, while FIGS. 10A, 10B, and 10C are corresponding side view illustrations showing incremental movement of valve 920 within shunt 902 when AV shunt assembly 900 is disposed in vivo with shunt body 904 extending between an artery A and an adjacent vein V. Blood flow BF is indicated in the figures with directional arrows. It should be noted that FIGS. 9A, 9B, 9C, 10A, 10B and 10C are also representative illustrations of the incremental valve positions that are possible for AV shunt 100 discussed above. In shunt assembly 900, tubular body 904 of shunt 902 may be a polymeric or metal cylinder having a hollow bore therethrough and being radially incompressible or unexpandable in comparison to the plain stent or a stent-graft as described above with respect to shunt bodies 104, 304. Shunt 902 also includes a plurality of anchors 910 radially extending from each end of shunt body 904. Valve 920 has a tubular body 926 defining a lumen 927 therethrough that is closed on each end by end caps 922, which may be larger in diameter than body 926, as shown in FIG. 10A, or may be the same diameter as body 926, as shown in FIG. 9A. Valve body 926 may be a polymeric or metal cylinder that is, like body 904, radially incompressible or unexpandable in comparison to valve body 120 described above with respect to AV shunt assembly 100. Thus, although anchors 910 are folded down against valve body 926 when the shunt assembly 900 is in a low-profile delivery configuration, shunt body 904 and valve 920 are not radially compressed for delivery.

FIG. 9A illustrates a first closed position of valve 920 in which a first end cap 922 abuts against first end 906 of shunt body 904. As shown in the corresponding in vivo illustration FIG. 10A, shunt body 904 is disposed between artery A and vein V with anchors 910 radially extending from shunt body 904 and pressing against adjacent vessel walls of artery A and vein V. With no part of orifices 928 extending out of shunt body 904 into artery A, blood in artery A is not permitted to flow into shunt 902. Valve 920 extends into vein V such that portions of orifices 928 are exposed to blood in vein V. While blood in vein V can flow through orifices 928 into and out of valve lumen 927 in valve body 926, there is no intermixing of arterial and venous blood because blood in artery A is not permitted to flow into shunt 902 when valve 920 is in the first closed valve position.

FIGS. 9B and 10B illustrate an open position in which portions of orifices 928 extend beyond first and second ends 906, 908 of shunt body 904 into both artery A and vein V. Blood within artery A is thus permitted to flow into orifices 928, through valve lumen 927, and out of orifices 928 into vein V. More particularly, the portion of the blood flow passageway within shunt 902 is defined by lumen 927 extending through valve body 926 and the portions of orifices 928 that are closed on their exterior sides by the surrounding shunt body 904. Thus the entire blood flow passageway of AV shunt assembly 900 is a combination of the total orifice area exposed in artery A, the blood flow passageway within shunt 902, and the total orifice area exposed in vein V. As is known by one of ordinary skill in the art, when circulating through a body with no AV shunts in place, oxygenated blood flows away from the heart to the tissue through arteries and capillaries and then following the release of oxygen in the tissues, the blood returns in veins to the heart. Arterial blood has a higher blood pressure than blood in veins. When an AV shunt is in place, the blood pressure difference causes some arterial blood to bypass the capillaries and tissues and instead be diverted into the vein to return to the heart. Accordingly, as shown in FIG. 10B, AV shunt assembly 900 having valve 920 in an open position diverts some arterial blood into the vein V.

FIGS. 9C and 10C illustrate a second closed position of valve 920 in which second end cap 922 abuts against second end 908 of shunt body 904. With no part of orifices 928 extending out of shunt body 904 into vein V, blood in vein V is not permitted to flow into shunt 902. Valve 920 extends into artery A such that portions of orifices 928 are exposed to blood in artery A. While blood in artery A can flow through orifices 928 into and out of valve lumen 927 in valve body 926, there is no intermixing of arterial and venous blood because blood in artery A is not permitted to flow out of shunt 902 in to vein V when valve 920 is in the second closed valve position.

FIGS. 1, 9B, 10B and 14 illustrate shunt assemblies of the invention with valves in open positions that are approximately centered within respective shunts. As shown in these figures, the total area of the orifices exposed from the shunt body in the artery is approximately equal to the total area of the orifices exposed from the shunt body in the vein. This centered valve position may be considered to be a "fully open throttle" state providing maximum possible blood flow rate through the shunt assembly under any given set of patient hemodynamic conditions. Preferably, the transverse cross-sectional area of the shunt lumen is larger than the total area of the orifices exposed from either end of the shunt body in the maximum flow position of the valve such that the shunt lumen presents negligible restriction in the flow path through the shunt assembly. In comparison to the fully open throttle state shown, other valve positions that reduce the total orifice area exposed from the shunt body in either the artery or the vein will tend to provide reduced blood flow through the shunt assembly by restricting either inflow from the artery or outflow into the vein. Thus, in valve positions where the total orifice area exposed from the shunt body in one vessel is different from the total orifice area exposed from the shunt body in the other vessel, the regulating effect on the flow of oxygenated arterial blood through the shunt assembly into the vein is dependent on the flow restriction caused by the lower of the two total exposed orifice areas.

Figure 16:
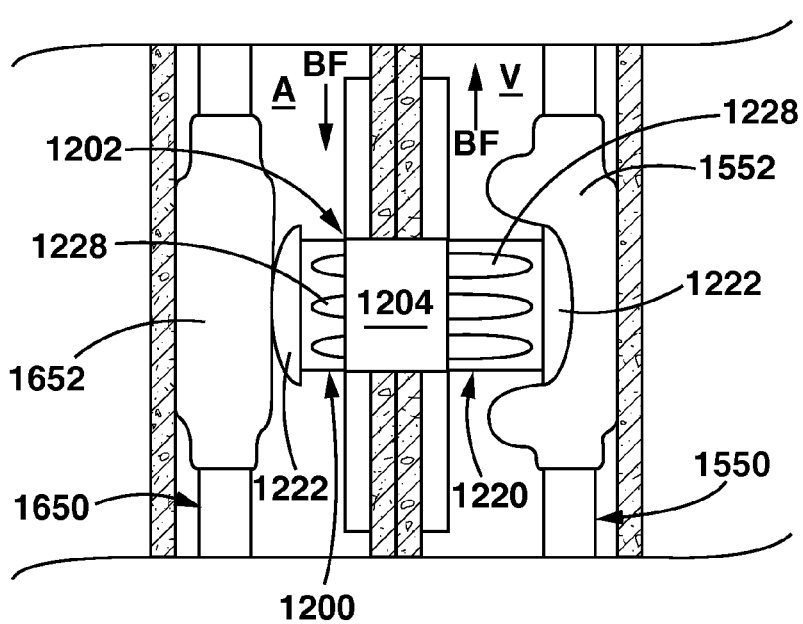

It will be understood by one of ordinary skill in the art that various incremental open positions of valve 920 may be achieved as valve 920 moves from the first closed position of FIGS. 9A and 10A or the second closed position of FIGS. 9C and 10C to the central, fully open throttle position of FIGS. 9B and 10B. FIG. 16 may be considered to illustrate a partially open valve position for valve 1220 wherein the blood flow rate through shunt assembly 1200 is controlled by the total orifice area exposed from the shunt body 1204 in artery A. For valve bodies having generally symmetrical orifice arrangements as illustrated, the blood flow through shunt 902 may be regulated by controlling the length of valve body 926 that is permitted to extend into artery A or vein V. However, the invention is not on limited, and various alternatives in the number, length, shape, pattern and arrangement of orifices in the valve body are possible and may result in a non-linear relationship between the length of the valve body exposed from the shunt and the flow rate through the shunt assembly.

The physician may incrementally adjust the longitudinal position of valve 920 relative to shunt 902 in order to increase or decrease blood flow through AV shunt assembly 900 as necessary in order to optimize performance of AV shunt assembly 900. For example, if additional improvement of blood oxygenation is necessary or desirable, valve 920 is shifted to increase the flow of oxygenated blood through the shunt assembly from artery A to vein V. After adjustment, the patient's blood oxygenation may be measured again to determine changes therein due to the valve position adjustment and a determination may then be made whether additional adjustment(s) are necessary or desirable. The friction fit of valve 920 within shunt 902 is sufficient to hold the adjusted position indefinitely, while permitting future adjustments as discussed below.

In an embodiment, longitudinal shifting of the valve within the shunt may be accomplished in vivo by inflating a catheter balloon. More particularly, with reference to FIGS. 11-16, a method of forming a connection between an artery A and an adjacent vein V and controlling blood flow through the connection is shown. Blood flow BF is indicated in the figures with directional arrows. In one embodiment, artery A and vein V are the femoral artery and femoral vein of a patient's leg. However, embodiments hereof may be deployed in any two adjacent body lumens or cavities in which it is desirable to form a connection having an adjustable rate of fluid flow therethrough.

Figure 11:
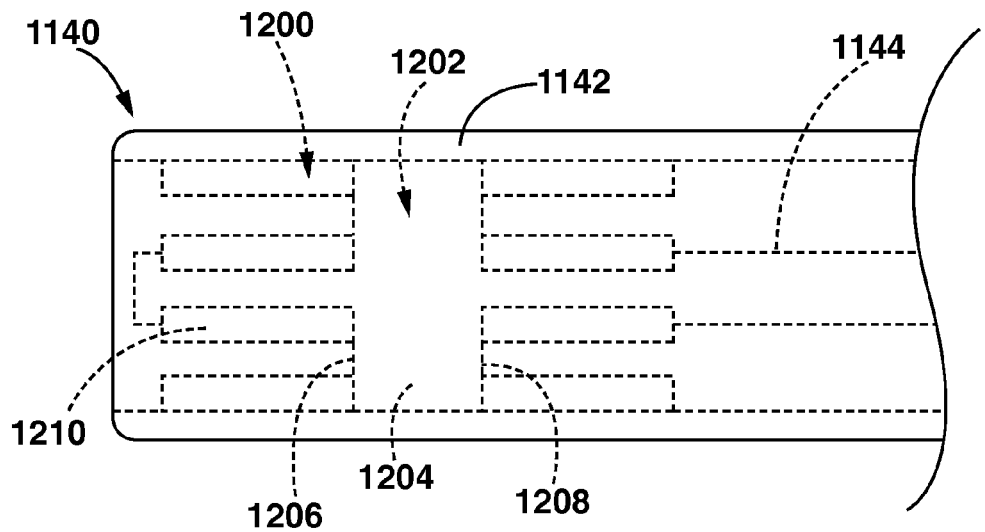
FIGS. 11-16 illustrate a method of forming a connection between an artery A and an adjacent vein V and controlling blood flow through the connection according to another embodiment of the invention.

FIG. 11 is a side view illustration of a distal end of delivery system 1140 showing in phantom an AV shunt assembly 1200 in its radially compressed delivery configuration. AV shunt delivery system 1140 includes a retractable sheath 1142 and a catheter 1144. AV shunt assembly 1200 is mounted about the distal end of catheter 1144 and sheath 1142 surrounds and constrains shunt assembly 1200 in the delivery configuration. Sheath 1142 also isolates AV shunt assembly 1200 from the vasculature being traversed during delivery. As shown in FIG. 11, when compressed within sheath 1142, anchors 1210 are substantially straightened to distally and proximally extend from first and second ends 1206, 1208, respectively, of tubular body 1204 of shunt 1202. Catheter 1144 may be fitted with a variety of arrangements to load and retain the collapsed shunt, and to advance or retract the shunt within sheath 1142 to complete or abort delivery of the shunt.

Figure 11A:
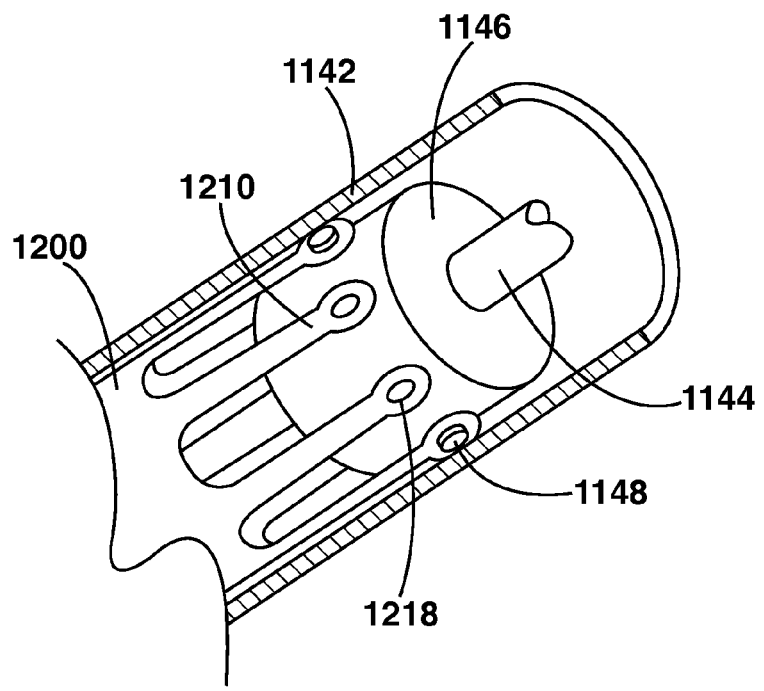
Figure 11B:
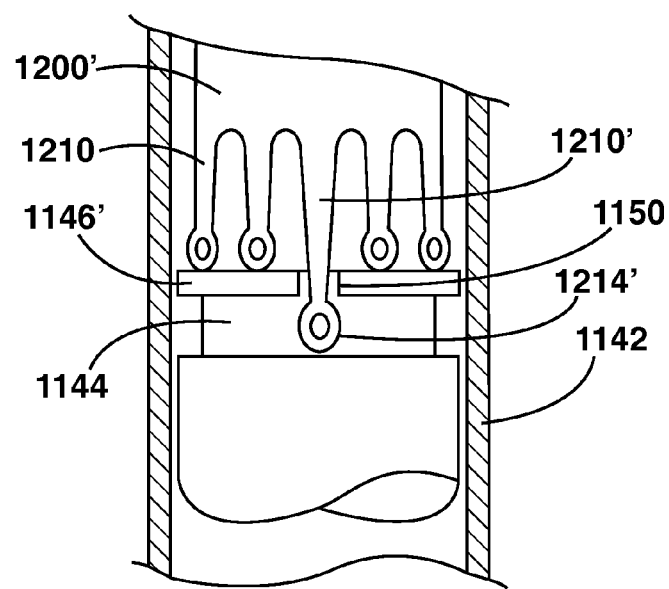

In an embodiment shown in FIG. 11A, catheter 1144 may include a retainer 1146 dimensioned to span the interior space between two or more straightened anchors 1210 and including one or more retention pins 1148 to engage corresponding eyelets 1218 to temporarily secure one end of AV shunt assembly 1200 onto catheter 1144. In an embodiment shown in FIG. 11B, catheter 1144 may include a disk-shaped retainer 1146' dimensioned to span the inside diameter of sheath 1142 and including a slot 1150 for receiving an elongated anchor 1210'. In the delivery configuration, AV shunt assembly 1200' is mounted adjacent retainer 1146' such that anchors 1210 are disposed on one side of the retainer and anchor tip 1214' of elongated anchor 1210' is disposed on the opposite side of the retainer. In another example, the retainer may include an end stent capture configuration as described in U.S. Patent Pub. 2009/0276027 to Glynn, which is hereby incorporated by reference herein in its entirety. Valve 1220, which is shown starting in FIG. 13 but obscured from view in FIG. 11, is disposed to extend within shunt body 1204 and anchors 1210 in a delivery configuration.

Figure 12:
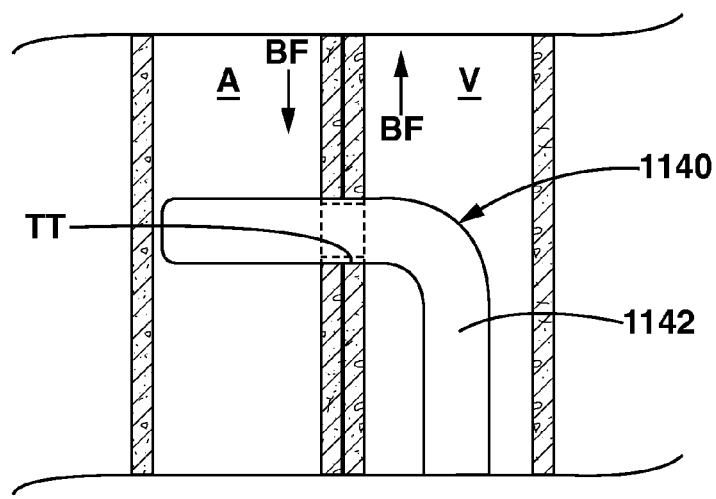

With reference to FIG. 12, an AV shunt delivery system 1140 is shown after having been introduced into the vasculature via a percutaneous entry point formed in the femoral vein, via e.g., the Seldinger technique. AV shunt delivery system 1140 is tracked through the femoral vein to a target location at which an AV fistula or connection is to be formed. Delivery system 1140 may be modified to create a tissue track TT, or tissue track TT may have been previously formed by a separate tissue penetrating catheter device (not shown) as would be known to one of skill in the art. Tissue track TT extends through the wall of vein V, through any intervening tissue and/or hollow space between vein V and artery A, and through the wall of artery A to thereby extend between the lumens of vein V and artery A. The PIONEER catheter, commercially available from Medtronic CardioVascular, Inc., Santa Rosa, Calif., is a tissue penetrating catheter suitable for use in embodiments described herein. Optionally, one or more track modifying devices such as balloon catheters and/or atherectomy catheters may be used to enlarge, dilate, debulk, and/or bore the tissue track TT, after which they are removed. Examples of track modifying devices and procedures of this sort are provided in U.S. Pat. No. 5,830,222 to Makower and U.S. Pat. No. 6,561,998 to Roth et al., the disclosures of which are hereby incorporated by reference herein in their entireties. Referring again to FIG. 12, delivery system 1140 is advanced through tissue track TT until shunt body 1204 is approximately centered within tissue track TT such that unexpanded anchors 1210 of shunt 1202 extend distally and proximally into artery A and vein V, respectively. Although obscured from view, the first or distal end 1219 of valve 1220 extends into artery A and the second or proximal end 1221 of valve 1220 extends into vein V. The AV shunt assemblies of the invention are reversible, as is their method of implantation. E.g., a shunt assembly can be inserted into an artery and deployed in a tissue track from the arterial side to the venous side, and either end of the shunt assembly can be deployed in either vessel.

Figure 13:
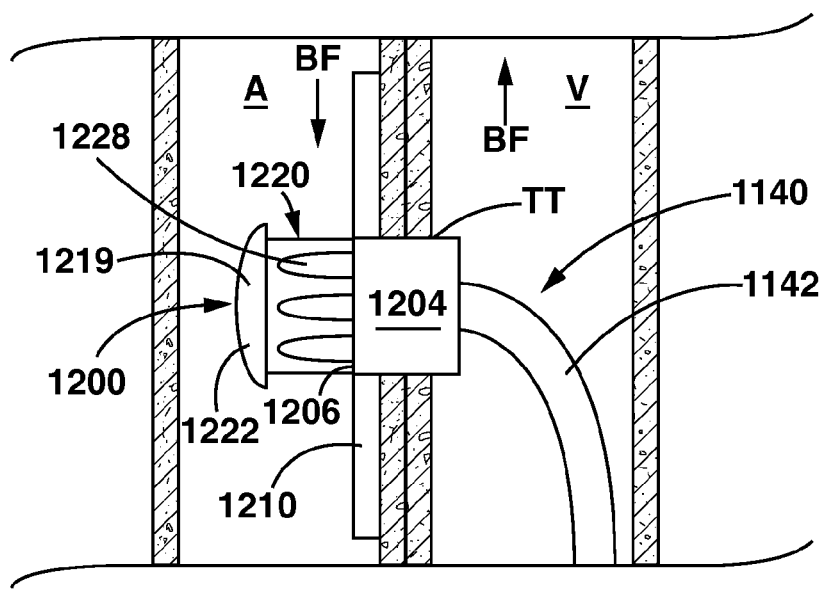

Referring now to FIG. 13, when AV shunt assembly 1200 is positioned as desired, sheath 1142 is proximally retracted in order to permit AV shunt assembly 1200 to expand. More particularly, anchors 1210 are released by retracting sheath 1142 by a sufficient amount that this portion of the prosthesis is exposed. Due to their self-expanding properties, anchors 1210 will expand radially outwardly relative to the sheath in which shunt assembly 1200 was enclosed. FIG. 13 shows sheath 1142 retracted a sufficient amount to allow self-expansion of shunt body 1204, anchors 1210 extending from first end 1206 of shunt body 1204 and the portions of valve 1220 released exteriorly of sheath 1142. In the partially deployed configuration shown, anchors 1210 extending from first end 1206 of shunt body 1204 radially expand against a vessel wall of artery A and shunt body 1204 radially expands within tissue track TT.

Figure 14:
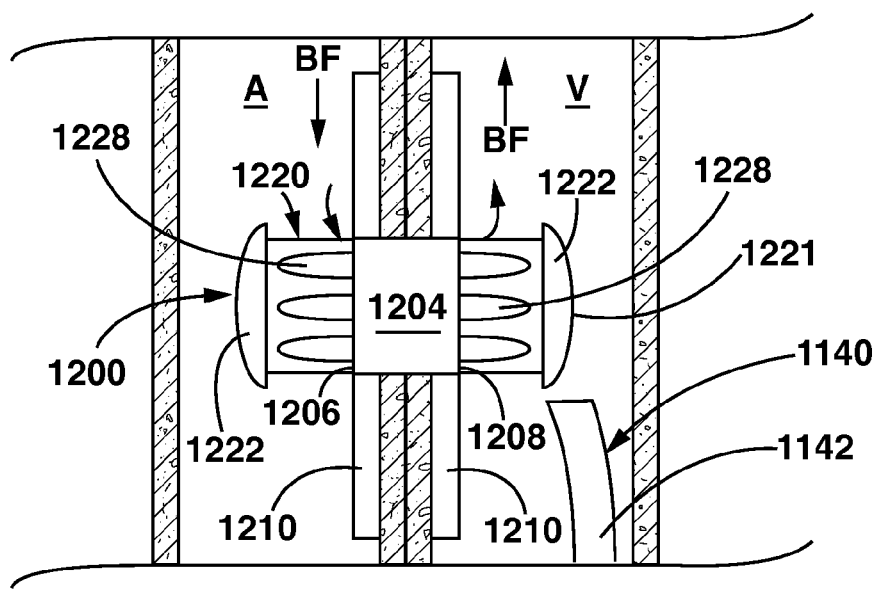

Sheath 1142 continues to be proximally retracted, as illustrated in FIG. 14, thus exposing and deploying anchors 1210 extending from second end 1208 of shunt body 1204 such that they radially expand against a wall of vein V. Proximal retraction of sheath 1142 continues until a proximal end of valve 1220 of AV shunt assembly 1200 is exposed and allowed to self-expand, thereby resulting in the uncoupling of the shunt assembly from catheter 1144. The delivery system 1140 can then be retracted from the patient, leaving the expanded AV shunt assembly 1200 deployed as shown in FIG. 14. The expanded AV shunt assembly creates a blood flow passageway or connection between artery A and vein V. FIG. 14 illustrates an open position of valve 1220, in which portions of orifices 1228 are exposed beyond shunt body 1204 in both artery A and vein V such that a portion of the blood within artery A is permitted to flow through orifices 1228 of shunt assembly 1200 and into vein V.

In an alternative method of delivery, AV shunt assembly 1200 may be separated into shunt 1202 and valve 1220, which are delivered sequentially. Once shunt 1202 is deployed in tissue track TT, valve 1220 may be delivered by the same or another system 1140 and released to self-expand within shunt 1202. Although such a method of delivery requires an additional step, each component may be collapsed to an advantageous delivery configuration having a lower profile than AV shunt assembly 1200.

In another variation of AV shunt assembly 900, shunt body 904 and valve 920 are not radially compressed for delivery although anchors 910 are folded down against valve body 926 when the shunt assembly 900 is in a low-profile delivery configuration. In such an arrangement, delivery system 1140 is larger in diameter than would be required for a radially compressible version of AV shunt assembly 900. Alternatively, an incompressible version of AV shunt assembly 900 may have smaller diameters for both shunt body 904 and valve 920 such that the maximum flow rate therethrough is less than that of the compressible version of AV shunt assembly 900. If a clinician judges that it would be advantageous to provide more fistular blood flow than is possible through an AV shunt assembly of the invention, then an additional AV shunt assembly can be implanted.

Figure 15:
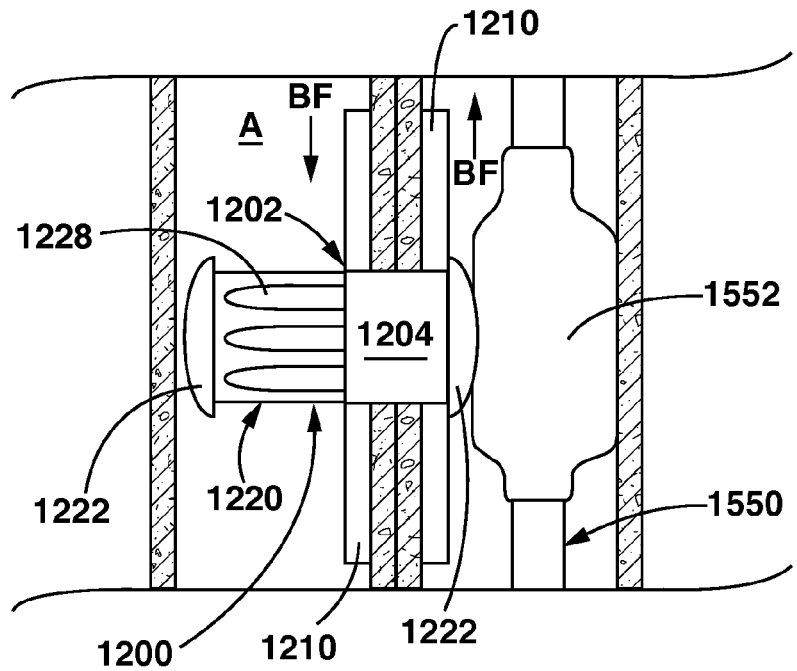

After AV shunt assembly 1200 is implanted, the flow therethrough may be adjusted in vivo. As described above with respect to FIGS. 9A-9C and FIGS. 10A-10C, in order to regulate the amount of blood flow through shunt assembly 1200, movable valve 1220 may be longitudinally shifted or translated relative to shunt body 1204 by applying a force against one of the first and second ends of valve 1220. As shown in FIG. 15, longitudinally shifting valve 1220 within the shunt 1202 may be accomplished by inflating a balloon 1552 of a balloon catheter 1550. Balloon 1552 has an expanded diameter equal or greater than the diameter of the target vessel, which in the illustrated embodiment is vein V. Balloon catheter 1550 may be percutaneously introduced and deployed within vein V, and balloon 1552 is inflated and expanded until the balloon contacts end cap 1222 and pushes valve 1220 in a direction towards artery A. If the physician desires to close valve 1220 to stop blood flow through the lumen of shunt assembly 1200, balloon 1552 is inflated until no portions of orifices 1228 are exposed in vein V and/or the contacted end cap 1222 is pushed against anchors 1210 as shown in FIG. 15. In one embodiment, valve 1220 and shunt 1202 may include one or more radiopaque markers (not shown) such that the relative positions thereof may be viewed under fluoroscopy before, during and after the valve position is adjusted within the shunt. For example, such radiopaque markers may be utilized to confirm when the valve is in a closed position. Alternatively, cessation of blood flow through shunt assembly 1200 can be determined or confirmed by fluoroscopically viewing injections of radiopaque contrast in the vicinity of the shunt assembly, as would be understood by one of skill in radiological catheterization techniques.

If a physician desires to re-open valve 1220 to permit blood flow through the lumen of shunt assembly 1200, balloon catheter 1550 or a second catheter 1650 having a balloon 1652 may be delivered and deployed within artery A as shown in FIG. 16. Balloon 1652 is inflated and expanded until the balloon impinges on end cap 1222 and pushes valve 1220 in a direction towards vein V. Valve 1220 is longitudinally translated within shunt 1202 until it is in an open position which allows the desired volume of blood flow through the shunt assembly. In one embodiment, balloon 1652 has an expanded diameter equal to or greater than the diameter of the target vessel, which in this case is artery A, and balloon 1652 is only partially inflated in order to position valve 1220 in a desired open position. It will be understood by one of ordinary skill in the art that the amount of balloon expansion may be varied to effectuate the desired amount of longitudinal shifting of valve 1220 to result in the desired rate of blood flow through the shunt. In another embodiment, balloon 1652 has an expanded diameter smaller than the target vessel, which in this case is artery A, and full expansion of balloon 1652 pushes valve 1220 into an open position.

Another method of adjusting valve 1220 is also illustrated in FIG. 16 wherein catheter balloon 1552 is positioned at one end of valve 1220 and catheter balloon 1652 is simultaneously positioned at the opposite end of valve 1220. The position of valve 1220 may be adjusted by controlling the relative inflation pressures in balloons 1552 and 1652 to apply differential forces against the opposite ends of valve. Such a method may be useful when the static friction force between valve 1220 and shunt body 1204 is significantly higher than the moving friction force between valve 1220 and shunt body 1204, as may result from tissue ingrowth or thrombus formation after an indwelling period of time. When adjusting the valve under such conditions, it may be more likely for the valve to suddenly release from one position and overshoot the intended open valve position.

Although FIG. 15 illustrates a balloon catheter inflated within vein V to close the valve and FIG. 16 illustrates a balloon catheter inflated within artery A to re-open the valve, it will be understood by one of ordinary skill in the art that a balloon catheter may be delivered and deployed within either the artery A or vein V to longitudinally adjust the position of valve 1220 within shunt 1202. For example, a balloon may be inflated within the artery A to close the valve and/or a balloon may be inflated within the vein V to re-open the valve. Further, it will be understood by one of ordinary skill in the art that various incremental or intermediary open positions of valve 1220 may be accomplished by partially inflating a balloon within either the artery A or vein V or by utilizing a balloon having an expanded diameter smaller than the target vessel within either the artery A or vein V. Conventional balloon catheters that may be used in the present invention include any type of catheter known in the art, including over-the-wire catheters, rapid-exchange catheters, fixed-wire catheters, and any other appropriate balloon catheters. Catheters having dilatation balloons such as those used for angioplasty are preferred, although catheters having more elastic occlusion balloons may also be useful with the invention.

FIG. 17 illustrates another embodiment of the invention wherein AV shunt assembly 1800 includes a poppet-type valve 1720 disposed within a shunt 1802. Shunt 1802 is similar to shunt 902 except that first and second ends 1806, 1808 of shunt body 1804 for positioning and/or anchoring the assembly within a tissue track are slightly flared rather than having extended arms 910. Tubular shunt body 1804 has a hollow bore 1805 extending between open ends 1806, 1808 and is a radially-expandable stent-graft constructed from a tubular stent 1807 and graft material 1809.

FIG. 18 illustrates valve 1720 including stem 1762 extending from an end cap or disk 1760 to an opposite end 1764. Stem 1762 may be a rod having a circular or other transverse cross-sectional shape. Stem end 1764 may be flared, enlarged and/or rounded for receiving stem translation force from an inflated catheter balloon with a reduced risk of puncturing a balloon used to adjust valve 1720. Valve stem 1762 may be stainless steel or other rigid metal or resin, and may not be radially compressible. Disk 1760 has a shape memory to return to the expanded configuration from a compressed, folded or constricted delivery configuration. Disk 1760 may be circular and generally flat or biconvex in shape and may be formed from a closed-cell foam or mesh-covered wire frame that substantially blocks blood flow therethrough.

Valve 1720 is moveably disposed within hollow bore 1805 of shunt 1802 and has a length $L_V$ that is longer than a length $L_S$ of shunt body 1804 such that, in the partially open valve position shown in FIG. 17, a first end 1764 of valve 1720 extends beyond first end 1806 of shunt body 1804 and a second end 1721 of valve 1720 extends beyond second end 1808 of shunt body 1804. Valve stem 1762 extends through hollow bore 1805 to define an annular shunt lumen 1827 between the outer surface of stem 1762 and the inner surface of shunt body 1804, as illustrated in FIG. 17A. In the deployed, expanded configuration of shunt assembly 1800, valve disk 1760 has a diameter $D_V$ that is greater than or equal to the diameter $D_S$ of shunt end 1808. When valve 1720 is in any of various open positions, valve disk 1760 is longitudinally spaced apart from shunt end 1808 to define an adjustable annular valve orifice 1728 therebetween. The blood flow passageway through shunt assembly 1800 is a combination of valve orifice 1728 and lumen 1827 through shunt 1802. When valve 1720 is in the closed position, as shown in FIG. 20, valve disk 1760 is disposed in sealing contact with shunt end 1808 to effectively close orifice 1728.

Valve 1720 is also coupled to shunt body 1804 via at least one connector 1866 formed from a plastically deformable material such as, but not limited to, stainless steel, Although FIG. 17 shows a single connector 1866 attached between valve end 1721 and shunt end 1808, those of skill in the art would recognize possible variations such as a plurality of connectors 1866 arranged between valve end 1721 and shunt end 1808 and/or one or more connectors 1866 arranged between valve end 1764 and shunt end 1806. The ends of connectors 1866 may be attached by known means including but not limited to swaging, suturing or overmolding.

Referring to FIGS. 19 and 20, which illustrate valve 1720 in vivo in open and closed positions, respectively, valve 1720 may be longitudinally shifted or translated within shunt 1802 in order to regulate the amount of blood flow through shunt assembly 1800. Blood flow BF is indicated in the figures with directional arrows. When axial force is applied to disk 1760 in order to shift valve 1720 between the open position of FIG. 19 and the closed position of FIG. 20, one or more connectors 1866 plastically deform to retain the selected valve position. The longitudinal position of valve 1720 relative to shunt body 1804 may be adjusted by inflating a catheter balloon as described above with respect to FIGS. 15 and 16. In an embodiment, AV shunt assembly 1800 is initially deployed with valve 1720 in its fully open position with connector 1866 fully extended such that disk 1760 is spaced apart a maximum distance from second end 1808 of shunt body 1804 such that the area of annular valve orifice 1728 is the same or greater than the transverse cross-sectional area of annular shunt lumen 1827 to allow maximum blood flow through the assembly under any given set of patient hemodynamic conditions. If it is desired to partially close valve 1720 to reduce the rate of blood flow through shunt assembly 1800, a balloon catheter may be percutaneously introduced and deployed within vein V, and the balloon may be partially inflated until the balloon contacts and pushes disk 1760 to a desired partially open position wherein annular valve orifice 1728 has an area that is smaller than the cross-sectional area of shunt lumen 1827. As an alternative to partial inflation, a balloon having an expanded diameter smaller than the target vessel may be used, or as described above, balloons may be positioned at both ends of valve 1720 and their differential inflation pressures may be adjusted to reposition valve 1720. Since connector 1866 plastically deforms, valve 1720 remains in the selected position unless force is again applied thereto.

If the physician desires to completely close valve 1720 to thereby stop blood flow through AV shunt assembly 1800, a catheter balloon may be inflated until disk 1760 is pushed against second end 1808 of shunt body 1804. If the physician desires to re-open or increase blood flow through valve 1720, a catheter balloon may inflated in artery A until the balloon contacts and pushes against valve stem end 1764 to open annular orifice 1728, thereby increasing the blood flow through the bore of shunt 1802. When valve 1720 is axially translated within shunt body 1804 to change the flow area of orifice 1728 and thus adjust the rate of blood flow through shunt assembly 1800, connector 1866 is plastically deformed and is sufficiently stiff to hold whatever position is selected. Alternatively, shunt assembly 1800 may be deployed in a reversed position from that illustrated, i.e., wherein valve disk 1760 and shunt body end 1808 are disposed in artery A instead of in vein V. The balloon-adjustable shunt assemblies of the invention may be implanted either surgically or transluminally, and from either the arterial or venous side of the fistula being formed.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An arteriovenous shunt assembly comprising:
    a tubular shunt having a hollow bore extending between first and second open ends thereof;
    a valve being disposed within the hollow bore of the shunt and having first and second valve ends extending from respective first and second shunt ends; and
    means for maintaining a longitudinal position of the valve relative to the shunt;
    wherein the position of the valve may be selectively and incrementally changed between a closed valve position and a maximum flow valve position to thereby adjust a rate of blood flow through the shunt.

2. The arteriovenous shunt assembly of claim 1, wherein the valve includes:

a cylindrical valve body sized to have a slidable friction fit within the shunt bore;
a lumen extending between closed first and second ends of the valve body; and
one or more valve orifices formed in the valve body to provide fluid communication with the valve lumen from outside the valve body;
wherein the one or more orifices are sized and shaped such that when the valve is in an open position the one or more orifices are uncovered adjacent both the first and second valve ends.

3. The arteriovenous shunt assembly of claim 2, wherein when the valve is in a closed position all of the one or more orifices adjacent one of the first and second valve ends are covered by the shunt.

4. The arteriovenous shunt assembly of claim 2, wherein the valve body lumen is a cylindrical bore or a trough.

5. The arteriovenous shunt assembly of claim 2, wherein the one or more valve orifices include a longitudinal slot.

6. The arteriovenous shunt assembly of claim 1, wherein the shunt further includes a plurality of anchors extending radially outward from at least one of the first and second ends thereof.

7. The arteriovenous shunt assembly of claim 1, wherein at least one of the first and second valve ends further includes a cap having a greater outer diameter than an outer diameter of the shunt.

8. The arteriovenous shunt assembly of claim 7, wherein the cap is dome shaped and coupled to one of the first end and second valve ends.

9. The arteriovenous shunt assembly of claim 7, wherein at least one of the first and second end caps includes at least one curved flow directing element extending therefrom into the valve body lumen.

10. The arteriovenous shunt assembly of claim 1, wherein the shunt and the valve are radially self-expandable.

11. The arteriovenous shunt assembly of claim 1 further including:
an elongate valve stem extending through the hollow bore to define an annular lumen between an outer surface of the stem and an inner surface of the shunt;
a circular valve disk coaxially mounted to the stem at the first end of the valve, the disk having a diameter equal to or greater than a diameter of the first end of the shunt; and
a plastically deformable connector coupling the valve to the shunt to maintain a selected position of the valve relative to the shunt;
wherein, in an open valve position the disk is longitudinally spaced apart from the first end of the shunt to define an annular orifice therebetween.

12. The arteriovenous shunt assembly of claim 11, wherein when the valve is in a closed position the disk is sealing pressed against the first end of the shunt.

13. The arteriovenous shunt assembly of claim 11, wherein the disk is formed of a mesh-covered wire frame that substantially blocks flow therethrough.

14. A method for forming a fluid connection having an adjustable flow rate between adjacent first and second blood vessels, the method comprising the steps of:
receiving a shunt assembly including:
a tubular shunt that defines a hollow bore between open first and second ends thereof;
a valve movably disposed within the shunt, the valve having a first end that extends beyond the first end of the tubular shunt and a second end that extends beyond the second end of the tubular shunt; and
means for maintaining a longitudinal position of the valve relative to the shunt;
delivering the shunt assembly intravascularly into a tissue track formed between the first and second vessels to a position where the first end of the valve is in the first vessel, the second end of the valve is in the second vessel, and the tubular shunt extends through the tissue track; and
selectively applying a force to either the first or second end of the valve to longitudinally shift the valve from a first position relative to the shunt to a second position relative to the shunt wherein the first and second positions are associated with different rates of blood flow through the shunt assembly between the first and second blood vessels.

15. The method of claim 14, wherein the step of selectively applying a force to either the first or second end of the valve includes inflating a catheter balloon within either the first or the second vessel such that the balloon impinges on and pushes against either the first or second end of the valve.

16. The method of claim 14, wherein the first vessel is an artery and the second vessel is a vein adjacent to the artery.

17. The method of claim 16, wherein the artery is a femoral artery in a leg and the vein is a femoral vein in the leg, and the step of longitudinally shifting the valve provides treatment for COPD.

18. The method of claim 14, wherein each of the first and second ends of the shunt further includes a respective first and second set of anchors radially extending therefrom, and wherein the step of delivering the shunt assembly includes positioning the shunt assembly through the tissue track such that the first set of anchors will radially expand within the first vessel and the second set of anchors will radially expand within the second vessel with a tubular body of the shunt extending through the tissue track.

19. The method of claim 14, wherein the step of delivering the shunt assembly includes retracting a sheath of a delivery system.

20. The method of claim 14, wherein the step of selectively applying a force to either the first or second end of the valve includes inflating a catheter balloon within each of the first and the second vessels such that the balloons impinge on and push against the first and second ends of the valve with differential forces.

* * * * *